United States Patent [19]

Shudo

[11] Patent Number: 4,658,023

[45] Date of Patent: Apr. 14, 1987

[54] PORPHYRIN DERIVATIVES

[76] Inventor: Koichi Shudo, 2-chome 25, Mishuku-jutaku 6-102, Higashiyama, Meguro-ku, Tokyo, Japan

[21] Appl. No.: 589,281

[22] Filed: Mar. 14, 1984

[30] Foreign Application Priority Data

Mar. 14, 1983 [JP]  Japan .................................. 58-042072

[51] Int. Cl.$^4$ .................. C07D 487/22; C07D 519/00; A61K 31/555
[52] U.S. Cl. ...................................... 540/145; 546/82
[58] Field of Search ............................. 546/2; 540/145

[56] References Cited

PUBLICATIONS

Hashimoto et al, Chem. Abs. 99, 122139s, (1983).
Matsudo et al, in "Antitumor Antibiotics", (Carter, Ed.), vol. 63, pp. 191–210, (1978).
Lown, J. C. S. Chem. Comm., 1982, p. 1298.

*Primary Examiner*—Mark L. Berch
*Attorney, Agent, or Firm*—Sughrue, Mion, Zinn, Macpeak, and Seas

[57] ABSTRACT

Porphyrin derivatives containing a dipyrido[1,2-a:3',2'-d]imidazole moiety and a porphyrin moiety therein and metal complexes thereof are disclosed. These derivatives possess enhanced oxygen-dependent DNA cleaving ability and are effective as anititumer agents.

8 Claims, No Drawings

PORPHYRIN DERIVATIVES

BACKGROUND OF THE INVENTION

1. Field of the Invention

The present invention relates to porphyrin derivatives having the structure of binding a porphyrin moiety possessing various physiological functions with specific heterocyclic compounds or dipyrido[1,2-a:3',2'-d]imidazoles via a chain structure containing amino groups, and metal complex compounds thereof. These compounds are useful as pharmaceuticals.

2. Development of the Invention

An oxygen-dependent DNA cleavage is one of important mode of action for antitumor agents. The present inventors have discovered that porphyrin derivatives represented by general formula (I) described hereinafter possess enhanced oxygen-dependent DNA cleaving ability and are quite effective as antitumor agents which can be administered orally or parenterally.

SUMMARY OF THE INVENTION

The porphyrin derivatives of the present invention are represented by general formula (I):

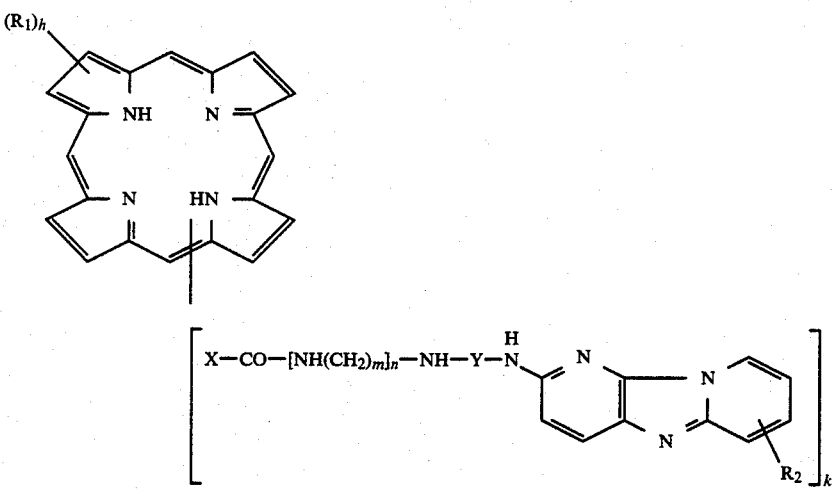

wherein $R_1$ represents a lower alkyl group, $-CH=CH_2$, $-CH_2CH_2CO_2H$, a substituted or unsubstituted aryl group; h represents 0 to 8 wherein, when h is not smaller than 2, $R_1$ each may be the same or different; X represents

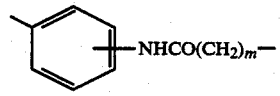

or $-CH_2CH_2-$; m represents an integer of 2 to 4; n represents 0 to 4; Y represents $-(CH_2)_l-$ or $-CO-(CH_2)_l-CO-$ wherein l represents an integer of 2 to 5; $R_2$ represents H or a lower alkyl group; and k represents an integer of 1 to 4.

The present invention also relates to metal complex compounds of the porphyrin derivatives represented by general formula (I) above.

DESCRIPTION OF THE PREFERRED EMBODIMENTS

The lower alkyl group shown by $R_1$ or $R_2$ means an alkyl group having 1 to 4 carbon atoms. Of the lower alkyl group shown by $R_1$, $-CH_3$ is particularly preferred.

Typical examples of the substituents of the substituted aryl group shown by $R_1$ include an alkyl group having 1 to 4 carbon atoms, a halogen atom, etc.

Of the porphyrin derivatives and metal complex compounds thereof in accordance with the present invention, $Fe^{III}$- or $Cu^{II}$-complex compounds of the porphyrin derivatives shown by general formula (I) wherein h is 3 to 7, X is $-CH_2CH_2-$ or

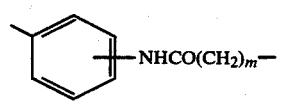

wherein the substituent $-NHCO(CH_2)_m-$ is located at the ortho- or para-position, n is 0 or 3 and, m and k each represents 2, are particularly advantageous in terms of preparation and can be advantageously employed as pharmaceuticals.

(I)

The porphyrin derivatives of the present invention can easily be synthesized in a conventional manner, e.g., by a process which comprises reacting porphyrin carboxylic acid derivatives represented by general formula (II):

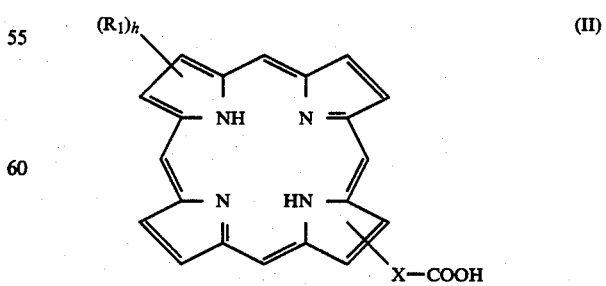

wherein $R_1$, h and X have the same significances as described above, with dipyridoimidazole derivatives represented by general formula (III):

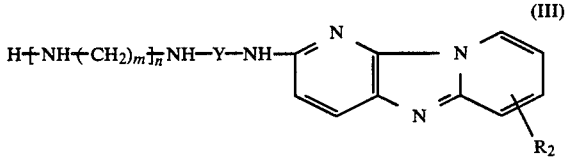

wherein Y, $R_2$, n and m have the same significances as described above, in a manner conventionally used for the formation of amide bond; more specifically, by reacting (II) with (III) generally at room temperature in a non-protonic solvent, e.g., dimethyformamide (DMF), dioxane, etc. using a condensing agent such s dicyclohexylcarbodiimide (DCC), N,N-carbonyldiimidazole, dicyclohexylcarbodiimide-N-hydroxysuccinimide, hydroxybenztriazole-DCC, etc. The resulting products can be separated by chromatography using silica gel or alumina followed by purification through recrystallization or reprecipitation.

Among the porphyrin carboxylic acid derivatives of general formula (II) described above, deuteroporphyrin and protoporphyrin are known compounds but some of tetraphenylporphyrin derivatives are novel. These novel compounds can also be prepared in a manner similar to these known compounds.

The dipyridoimidazole derivatives represented by general formula (III) can easily be prepared from 2-aminodipyridoimidazoles of general formula (IV):

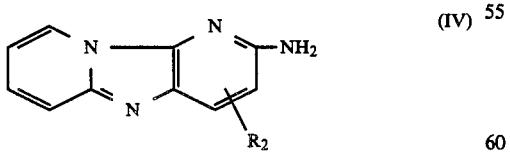

wherein $R_2$ has the same significance as described above, in a conventional manner. That is, heating of 2-aminodipyridoimidazoles with, for example, 3-bromopropylamine hydrobromide gives compounds of general formula (III) wherein m is 0 and Y is $-CH_2CH_2CH_2-$. Further, the reaction of 2-aminodipyridoimidazoles of general formula (IV) with succinic anhydride and then with amines such as spermine, spermidine or the like in the presence of a condensing agent such as N,N-carbonyldiimidazole, etc. forms the amide bond to give compounds of general formula (III) wherein n is 2 or 3, m is 3 or 4 and Y is $-COCH_2CH_2CO-$.

With respect to porphyrin complex compounds, the aimed products can be obtained as they are, in case that metal ions are previously contained in porphyrin, for example, in case that hemin chloride or the like is employed as a raw material. Otherwise, porphyrin complex compounds can be obtained by dissolving compounds represented by formula (I) in solvents such as dimethylformamide, etc. followed by reacting with metal salts such as $FeCl_2$, $FeCl_3$, $CuCl_2$, etc. while heating.

Hereafter the present invention will be described in more detail with reference to the following examples wherein all percentages are parts by weight and the pressure is atmosperic, unless otherwise indicated.

EXAMPLE 1

Preparation of Porphyrin Derivative of Formula (I')

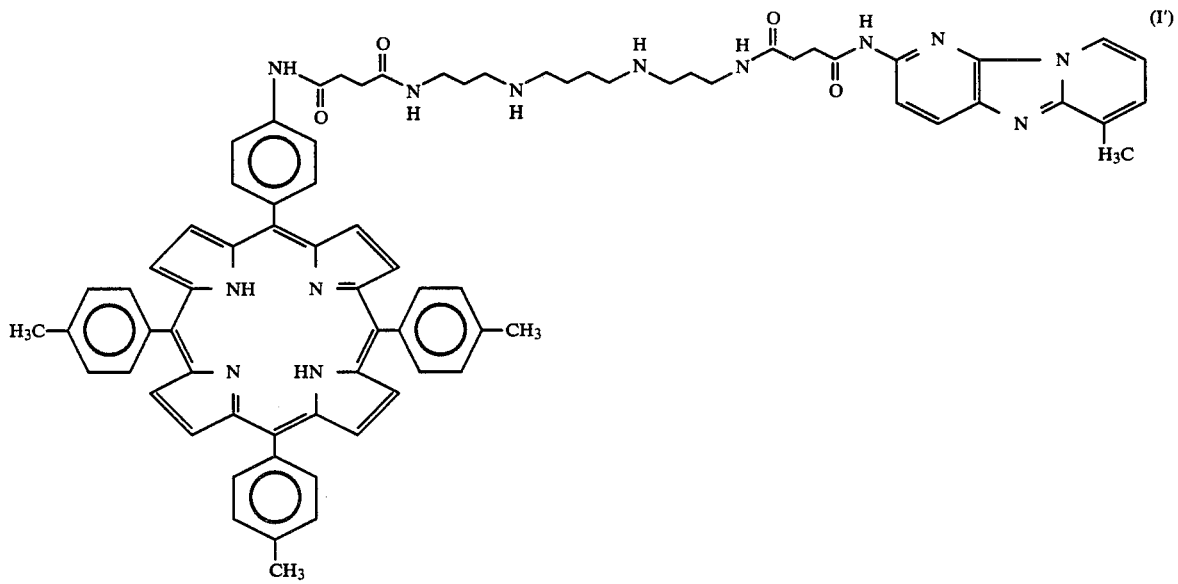

(a) Preparation of raw material (a), mesomono-p-anilino-tri-p-tolylporphyrin succinoyl derivative, shown by the following structure:

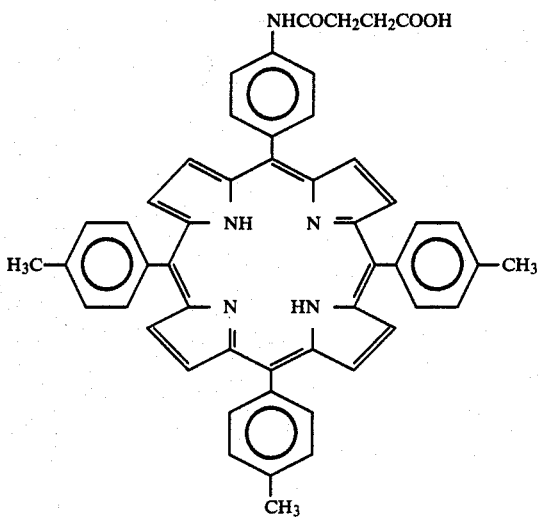

(a)

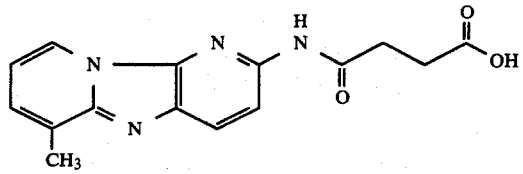

A mixture of p-tolualdehyde, p-nitrobenzaldehyde and pyrrole in a molar ratio of 2:1:3 was heated under reflux in acetic acid for 30 minutes. After cooling, the crystals precipitated were taken and dissolved in conc. hydrochloric acid. To the solution was added stannous chloride to effect reduction at 65° C. for 1 hour. The reaction liquid mixture was rendered alkaline with ammonia followed by extraction with methylene chloride. The extract was separated using a silica gel column. Recrystallization from benzene-chloroform gave the starting mesomono-p-anilino-tri-p-tolylporphyrin.

melting point >300° C.

$^1$H-NMR (COCl$_3$) ($\delta$): 2.70 (s, 9H), 7.04 (d, 8 Hz, 2H), 7.52 (d, 8 Hz, 6H), 7.95 (d, 8 Hz, 2H), 8.07 (d, 8 Hz, 6H), 8.81 (s, 4H), 8.82 (d, 4 Hz, 2H), 8.89 (d, 4 Hz, 2H).

|  | C | H | N |
|---|---|---|---|
| Found | 83.63 | 5.48 | 10.55 |
| Calcd. | 83.95 | 5.50 | 10.44 |

In 20 ml of chloroform was dissolved 50 mg of the thus obtained mesomono-p-anilino-tri-p-tolylporphyrin and 20 mg of succinic anhydride was added to the solution. The mixture was heated under reflux for 1 hour. Methanol was added to the reaction mixture to obtain 34 mg (yield: 59%) of mesomono-p-anilino-tri-p-tolylporphyrin succinoyl derivative by direct crystallization.

$^1$H-NMR (COCl$_3$) ($\delta$): 2.69 (s, 3H), 2.66 (s, 6H), 2.82 (br.s, 4H), 7.51 (d, 7 Hz, 4H), 8.06 (d, 7 Hz, 4H), 7.48 (d, 8 Hz, 2H), 8.04 (d, 8 Hz, 2H), 7.79 (d, 9 Hz, 2H), 8.10 (d, 9 Hz, 2H), 8.82 (br.s, 8H).

(b) Preparation of raw material (b):

To a solution of 900 mg of 2-amino-6-methyl-dipyrido[1,2-a:3′,2′-d]imidazole in 100 ml of ethyl acetate was added 500 mg of succinic anhydride. The mixture was heated under reflux. The precipitates formed after cooling were taken by filtration to obtain 600 mg (yield: 44%) of 2-succinoylamino-6-methyldipyrido[1,2-a:3′,2′-d]imidazole of formula below.

$^1$H-NMR (DMSO-d$_6$) ($\delta$): 2.52 (t, J=5 Hz), 2.56 (s, 3H), 2.69 (t, 5 Hz), 6.95 (t, 7 Hz), 7.36 (d, 7 Hz), 8.22 (d, 8 Hz), 8.32 (d, 8 Hz), 8.48 (d, 7 Hz).

Then 65 mg of the thus obtained dipyridoimidazole was dehydration-condensed with 160 mg of spermine in 5 ml of DMF in the presence of 32 mg of N,N′-carbonyldiimidazole. The reaction mixture was allowed to stand overnight to obtain as an oily substance 49 mg (yield: 47%) of raw material (b) shown by the structure:

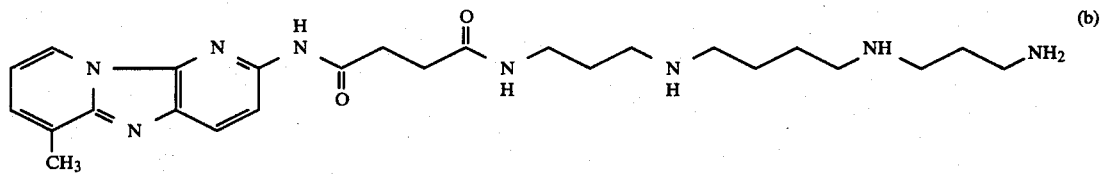

(b)

The characteristic data of this material (b) are as follows.

$^1$H-NMR (DMSO-d$_6$) ($\delta$): 1.30–1.60 (m), 2.18–2.30 (m): hydrogens of aliphatic group, 2.68 (s): hydrogens of methyl group, 8.20–8.24 (m): hydrogens of aromatic group.

(c) Thirty four (34) mg of the mesomono-p-anilino-tri-p-tolylporphyrin succinoyl derivative obtained in (a) described above was reacted with 9 mg of the raw material (b) obtained in (b) described above in 3 ml of DMF in the presence of 1.5 mg of N,N′-carbonyldiimidazole to obtain the crude product. After purification of the crude product by silica gel chromatography, the product was recrystallized from water-methanol to give 7 mg (yield: 72%) of the product.

| Elemental Analysis of Compound of formula (I).6H$_2$O | | | |
|---|---|---|---|
|  | C | H | N |
| Found | 65.06 | 5.97 | 14.82 |
| Calcd. | 64.78 | 6.29 | 14.87 |

UV Absorption: in CH$_2$Cl$_2$—10% MeOH: nm ($\epsilon$mM) 646 (5), 589 (5), 550 (10), 514 (25), 417 (180).

EXAMPLE 2

In 1 ml of DMF was dissolved 2 mg of the porphyrin derivative of formula (I′) obtained in Example 1. To the solution was added 10 mg of hydrous ferrous chloride. The mixture was reacted at 80° C. for 3 hours under de-airated condition to obtain the crude product of the iron complex shown below. The crude product was purified by alumina chromatography followed by reprecipitation from methanol-diluted hydrochloric acid. Melting point >300° C.

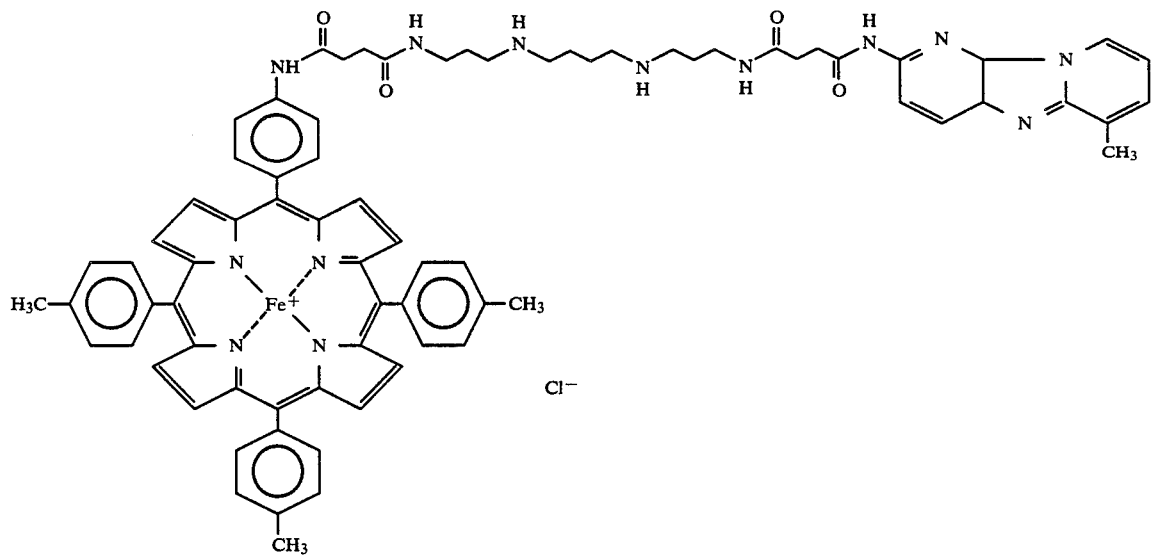
UV Absorption: in $CH_2Cl_2$—10% MeOH: mn (εmM) 668 (25), 505 (30), 445 (300).
EXAMPLE 3
Preparation of Porphyrin Derivatives Shown by Formulae (A) and (B):
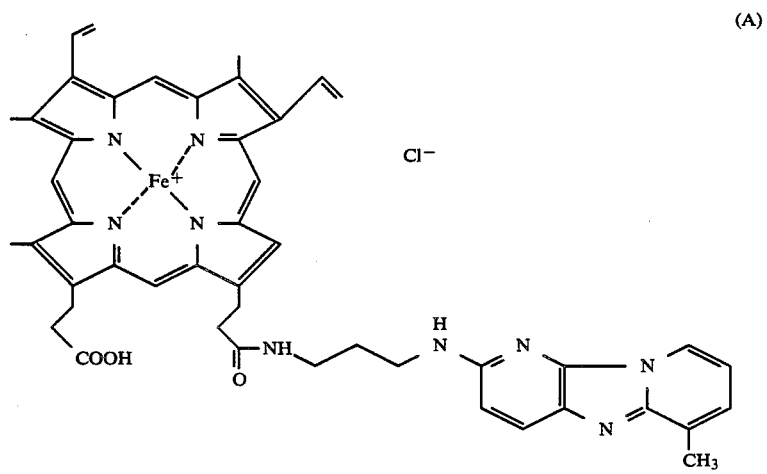
(A)
and -continued (B)

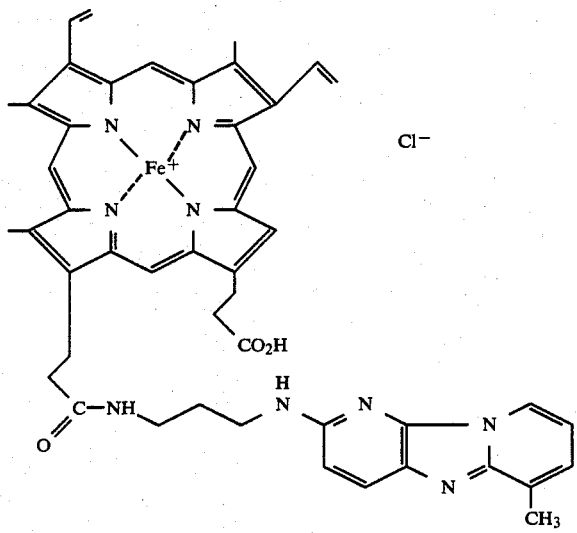

(a) Preparation of raw material (a):

Two hundred (200) mg of 2-amino-6-methyl-dipyrido[1,2-a:3′,2′-d]imidazole melted with 400 mg of 3-bromopropylamine hydrobromide at 180°–200° C. for 1 hour. After cooling, the product was isolated by extraction ((1) into an aqueous phase with a weak alkali-ethyl acetate (pH 7 to 8) and (2) into an organic phase with strongly alkaline KOH aq.-ethyl acetate). Recrystallization from ethanol-hydrobromic acid gave 130 mg (yield: 47%) of 2-(aminopropyl)amino-6-methyl-dipyrido[1,2-a:3′,2′-d]imidazole (raw material (a)) shown by the following formula:

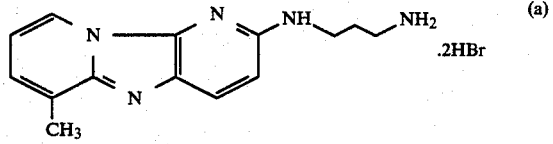

melting point: 283°–288° C.

$^1$H-NMR (CD$_3$OD) (δ): 2.10 (t-t, J=7 Hz), 2.70 (s, 3H), 3.15 (t, 7 Hz), 3.66 (t, 7 Hz), 7.03 (d, 10 Hz), 7.46 (t, 7 Hz), 7.92 (d, 7 Hz), 7.95 (d, 10 Hz), 8.94 (d, 7 Hz).

|  | Elemental Analysis | | |
| --- | --- | --- | --- |
|  | C | H | N |
| Found | 40.56 | 4.67 | 16.32 |
| Calcd. | 40.31 | 4.59 | 16.77 |

(b) In 15 ml of anhydrous pyridine was dissolved 350 mg of commercially available hemin chloride and 50 mg of pivalyl chloride was slowly added to the solution. To the mixture was added 120 mg of 2-(aminopropyl)amino-6-methyldipyrido[1,2-a:3′,2′-d]imidazole obtained in (a). The mixture was reacted at room temperature for 30 minutes and 100 ml of 3N hydrochloric acid was added to the reaction mixture. The formed precipitates were separated by silica gel Column chromatography to obtain a mixture of isomers shown by formulae A and B. The mixture was reprecipitated from pyridine-hydrochloric acid to obtain the isomeric mixture in the amount of 34 mg (yield: 11.3%).

UV Absorption: (in methanol, nm): 365 (sh), 388 nm, (in DMSO, nm, εmM): 620 (4), 498 (9), 404 (103).

$^1$H-NMR (DMSO-d$_6$): δ1.5 (br.), 7–8 (aromatic).

Mass spectrum (FAB): 856 (M$^+$ +1).

EXAMPLE 4

Two hundred and fifty (250) mg of hemin chloride was reacted with 100 mg of pivalyl chloride in 15 ml while heating to form the active ester. The active ester was reacted with 300 mg of 2-(aminopropyl)amino-6-methyldipyrido[1,2-a:3′,2′-d]imidazole obtained in Example 3(a) for 30 minutes to obtain the compound described below. The compound was purified by silica gel chromatography. Reprecipitation from pyridine-hydrochloride gave 24 mg (yield: 12%) of brown precipitates.

UV Absorption: (in methanol): 365 nm (sh), 388 nm, (in DMSO, nm, εmM): 625 (3), 500 (6), 401 (140).

Mass spectrum (FAB): 1093 (M$^+$ +1).

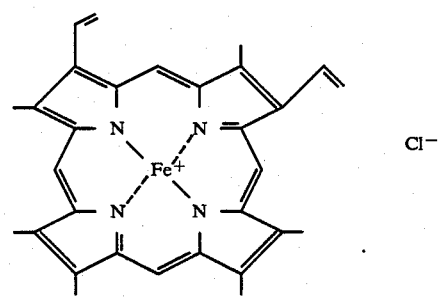

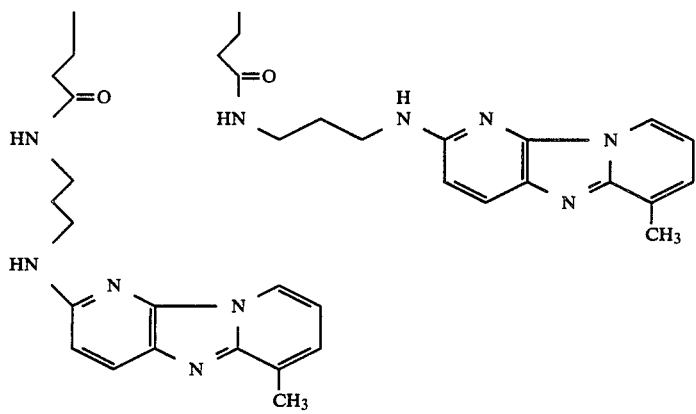

EXAMPLE 5

2-(Aminoethyl)amino-6-methyldipyrido[1,2-a:3',2'-d]-imidazole prepared in a manner similar to Example 3(a) was reacted with hemin chloride in a manner similar to Example 4 to give the crude product. The crude product was purified by silica gel chromatography (developed with ethyl acetate-methanol-ammonium hydroxide in a 8:2:0.8 molar ratio) to give the product shown below. Yield 12%.

Mass spectrum (FAB): 1065 ($M^+ + 1$).

By chromatography, the 1:1 reaction products of hemin chloride and the pyridoimidazole (which products correspond to the products shown by formulae A and B (l=2) obtained in Example (3) were obtained from fractions having higher polarity in the yield of 5%.

Mass spectrum (FAB): 842 ($M^+ + 1$)

EXAMPLE 6

2-(Aminobutyl)amino-6-methyldipyrido[1,2-a:3',2'-d]-imidazole prepared in a manner similar to Example 3(a) was reacted with hemin chloride in a manner similar to Example 4. The product was isolated by silica gel chromatography and reprecipitated from pyridine-hydrochloric acid to obtain a compound shown below in the yield of 10–15%.

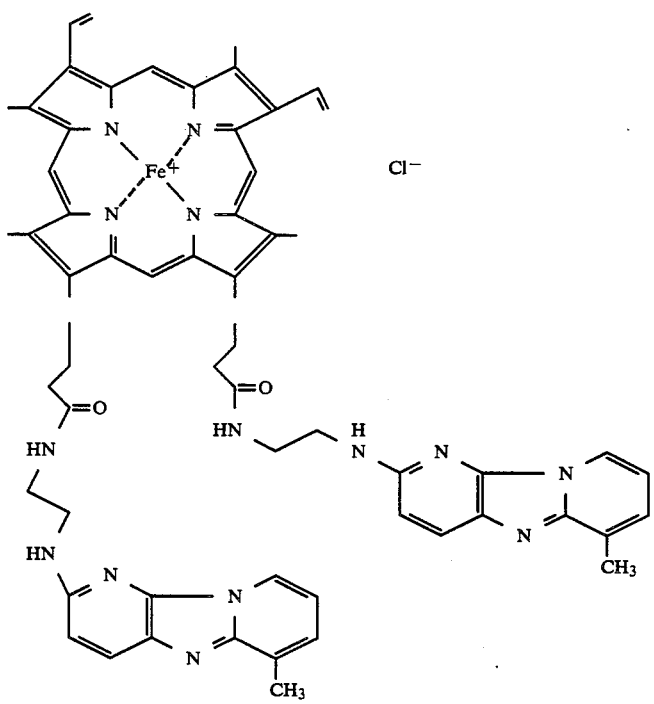

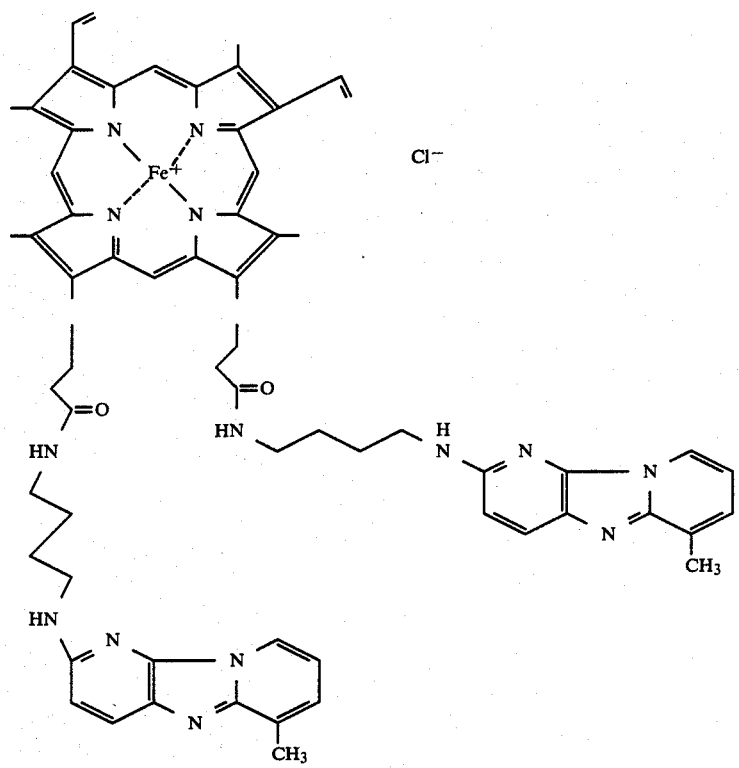

UV Absorption (in DMSO, nm, εmM): 624 (2.9). 501 (7.1), 400 (165).

|  | C | H | N |
|---|---|---|---|
| Calcd. | 51.82 | 5.46 | 13.22 |
| Found | 52.14 | 4.95 | 12.53 |

By chromatography, the 1:1 reaction products of hemine chloride and the pyridoimidazole (which products correspond to the products shown by formulae A and B (l=4) obtained in Example (3) were obtained from fractions having a higher polarity in the yield of 7%.

Mass spectrum (FAB): 870 (M+ +1).

While the invention has been described in detail and with reference to specific embodiments thereof, it will be apparent to one skilled in the art that various changes and modifications can be made therein without departing from the spirit and scope thereof.

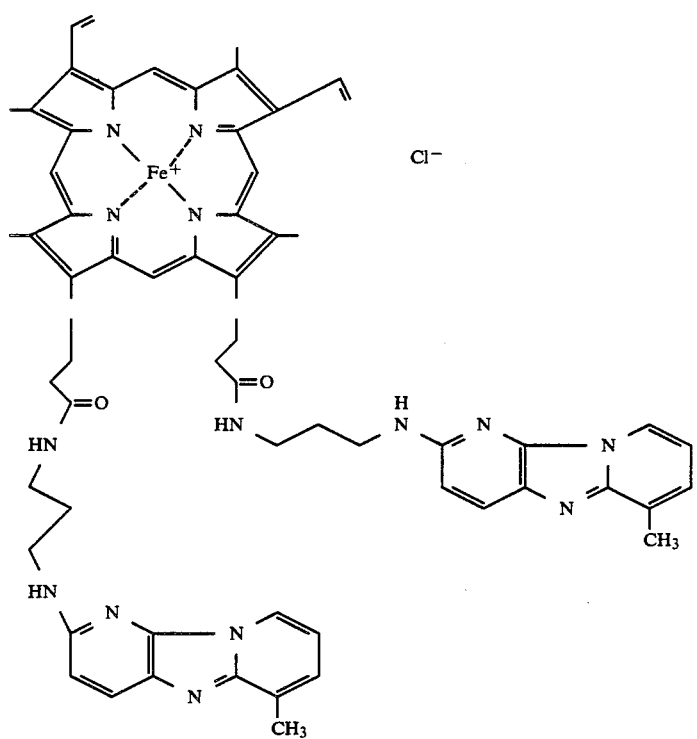
8. The metal complex compound which is shown by the following formula:
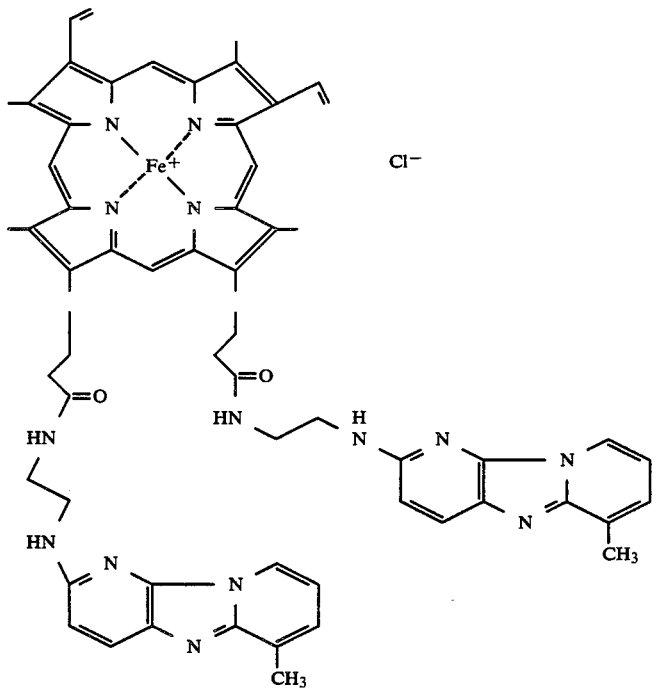

What is claimed is:

1. A metal complex compound comprising a metal complexed with a porphyrin derivative represented by formula (I):

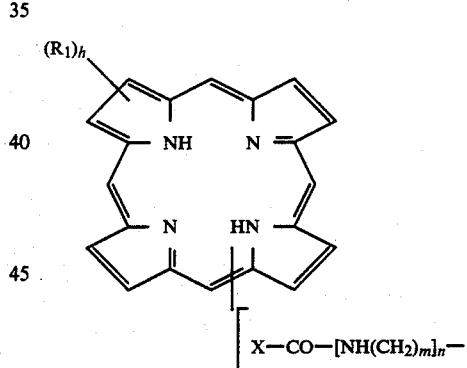

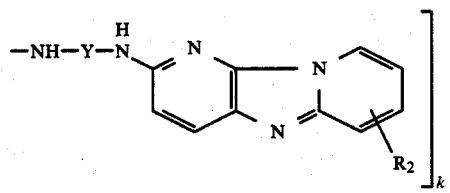

wherein $R^1$ represents a lower alkyl group, $-CH=CH_2$, $-CH_2CH_2CO_2H$, an aryl group or an aryl group substituted with an alkyl group having 1 to 4 carbon atoms or a halogen atom; h represents 0 to 8 wherein, when h is not smaller than 2, $R_1$ each may be the same or different; X represents

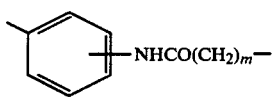

or —CH$_2$CH$_2$—; m represents an integer of 2 to 4; n represents 0 to 4; Y represents —(CH$_2$)$_l$— or —CO—(CH$_2$)$_l$—CO— wherein l represents an integer of 2 to 5; R$_2$ represents H or a lower alkyl group; and k represents an integer of 1 to 4 and any counterion pharmaceutically acceptable necessary for electrical neutrality.

2. The metal complex compound of a porphyrin derivative represented by general formula (I) as claimed in claim 1 wherein said metal complexed in the metal complex compound is selected from the group consisting of Fe$^{III}$ and Cu$^{II}$.

3. The metal complex compound of a porphyrin derivative represented by general formula (I) as claimed in claim 2 wherein h represents 3 to 7, X represents; when X is

the substituent —NHCO(CH$_2$)$_m$— is located at the ortho- or para-position; n represents 0 or 3 and, m and k each represents 2.

4. The metal complex compound which is shown by the following formula:

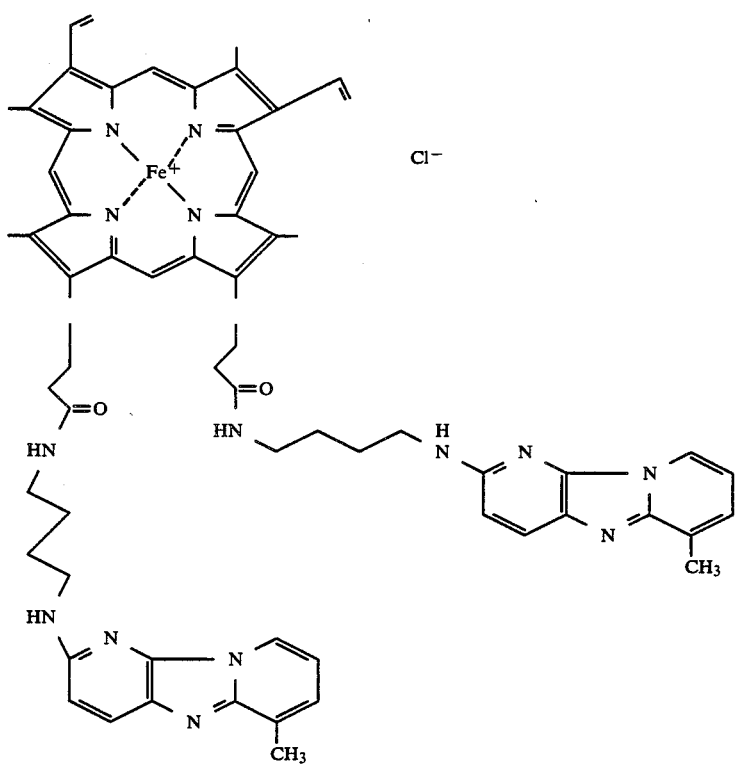

5. The metal complex compound which is shown by the following formula:

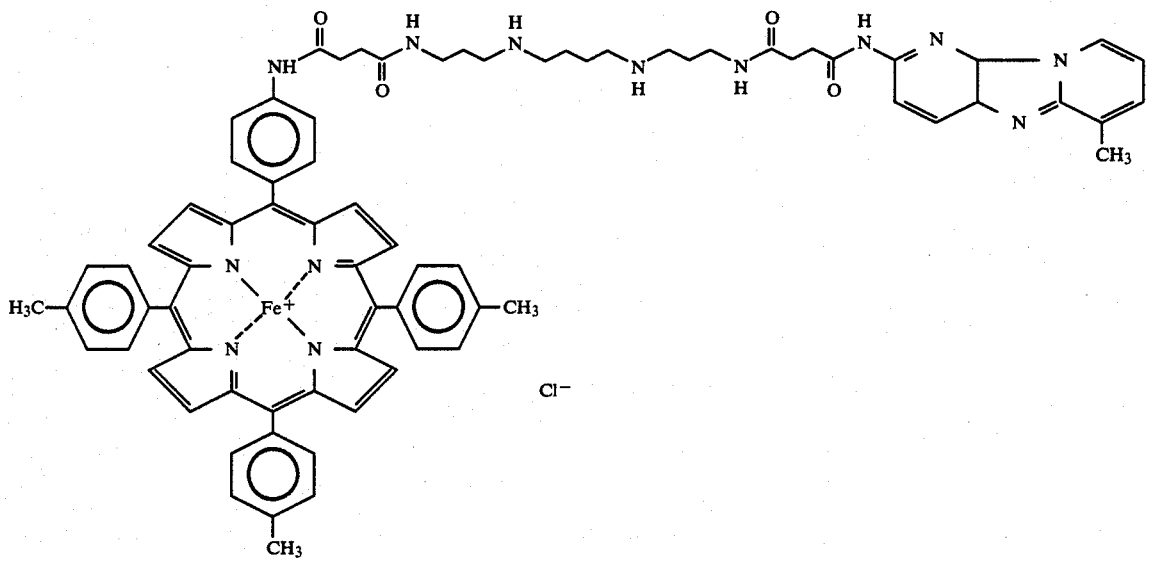
6. The metal complex compound which is a mixture of formulae (A) and (B) shown below:
wherein l represents an integer of 2 to 4.
7. The metal complex comopund which is represented by the following formula:
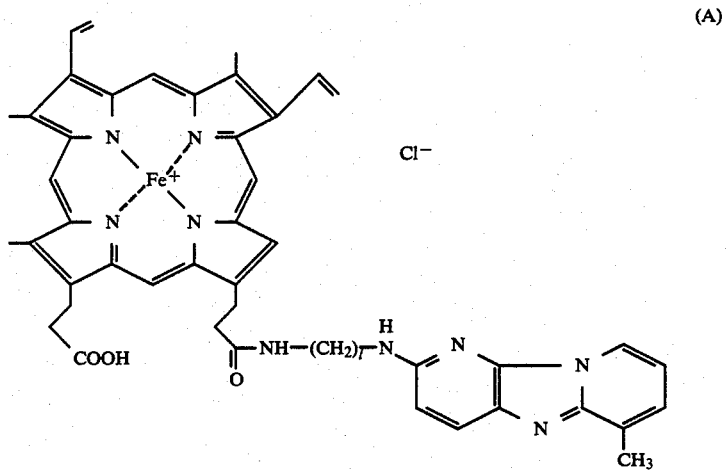
(A)
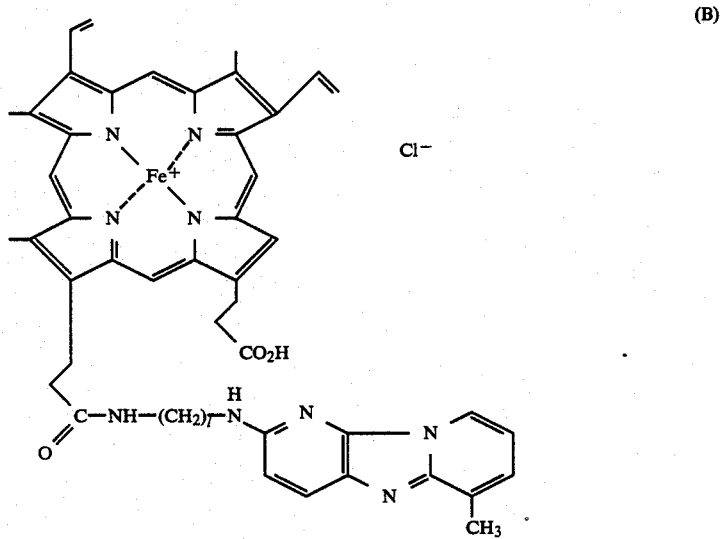
(B)